United States Patent [19]

Hannart

[11] 4,200,638
[45] Apr. 29, 1980

[54] INDOLE DERIVATIVES AND THERAPEUTICALLY ACTING DRUGS

[75] Inventor: Jean A. A. J. Hannart, Chaumont-Gistoux, Belgium

[73] Assignee: Omnium Chimique Societe Anonyme, Louvain-la-Neuve, Belgium

[21] Appl. No.: 946,456

[22] Filed: Sep. 27, 1978

[30] Foreign Application Priority Data

Sep. 30, 1977 [FR] France ................. 77 29574

[51] Int. Cl.² .................. A61K 31/44; D07D 471/04
[52] U.S. Cl. ...................................... 424/256; 546/66
[58] Field of Search ........................... 546/66; 424/256

[56] References Cited

PUBLICATIONS

Pinar et al., Chemical Abstracts, vol. 80 (1974) 60060f.

Primary Examiner—Richard Raymond

[57] ABSTRACT

The invention relates to new indole derivatives, their preparation and use as drugs.

Said compounds may be represented by the general formula

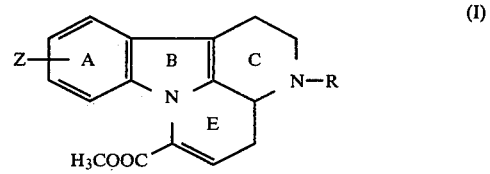

in which R represents a hydrogen atom or an alkyl or benzyl group and Z represents a hydrogen atom or a halogen atom or an alkyl, hydroxy, acyloxy, carbamate or methoxy group.

They are prepared by reacting tryptamine derivatives with synthons of the formula

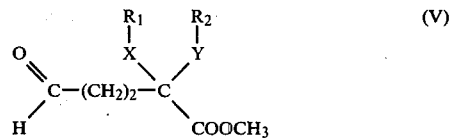

in which X and Y each represent an oxygen or sulphur atom, and $R_1$ and $R_2$ each represent an alkyl or phenyl radical or form together an alkylidene chain.

They may be used as intermediate compounds for chemical syntheses and also as drug for treating cerebro-vascular and cardio-circulatory insufficiencies.

5 Claims, No Drawings

INDOLE DERIVATIVES AND THERAPEUTICALLY ACTING DRUGS

The present invention relates to new indole derivatives of the general formula

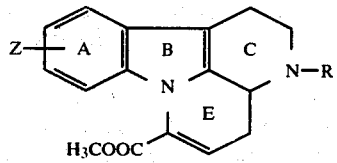

(I)

wherein R represents a hydrogen atom or a linear or branched saturated or unsaturated alkyl group having 1 to 5 carbon atoms or a benzyl (i.e. $CH_2$—$C_6H_5$) group, and Z represents either a hydrogen atom or an alkyl, hydroxy, acyloxy, carbamate or methoxy radical or a halogen atom.

The invention also relates to the preparation and use of said compounds as drugs.

The compounds I may be provided in the form of their bases or salts of addition with organic or inorganic acids. They may also be provided as optical isomers or as racemic mixtures of the corresponding bases or salts. All these forms are within the scope of the present invention.

The compounds I are structurally analogous to apovincamine, their molecule being formed by joining together four (namely A, B, C, E) of the five rings of apovincamine, which latter is represented by the formula:

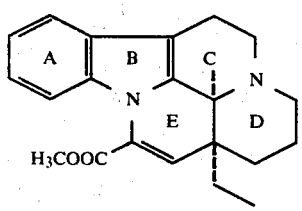

(II)

They will be named chanodesethylapovincamines.

They have the same skeleton as the compounds described in Applicant's French Pat. Nos. 7,625,802 and 7,716,546 or U.S. patent application Ser. No. 826,857 filed on Aug. 22, 1977 or British patent application 33,838/77 filed Aug. 12, 1977 and which are of the formula

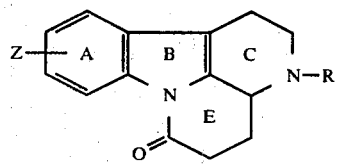

(III)

The compounds I, as the compounds II and III, have interesting therapeutical properties which will be described hereafter and are in addition valuable intermediate compounds for the synthesis of other compounds also having such properties.

The compounds I are prepared among others by condensing with a mono-substituted tryptamine of formula IV, in which Z and R have the above-indicated meanings, a synthon or aldehyde-ester of formula V:

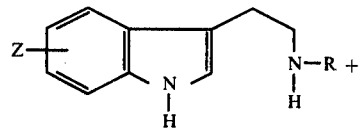

(IV)

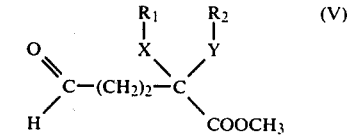

(V)

In formula V, X and Y each represent an oxygen or sulphur atom; $R_1$ and $R_2$ each represent an alkyl radical having 1 to 5 carbon atoms or form together an alkylidene chain having 2 to 3 carbon atoms, or represent a phenyl group.

According to one feature of the invention, condensation of compound IV with compound V under the conditions of the PICTET-SPENGLER reaction initially provides a tetrahydro-β-carboline VI which in a second step is subjected to an acid hydrolysis to obtain a compound VII which, under the conditions used, spontaneously is cyclized to give a chanodesethylvincamine VIII which is dehydrated to the compounds I of the invention, as shown hereafter.

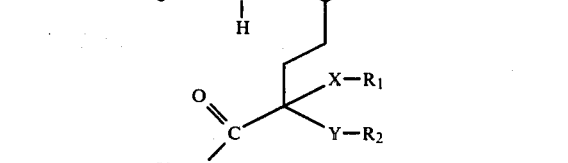

(VI)

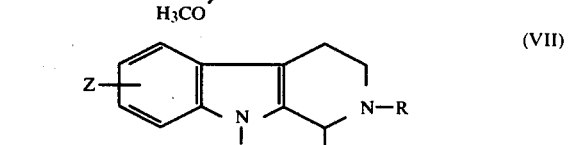

(VII)

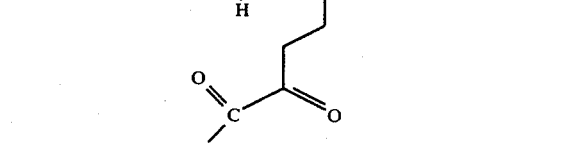

(VIII)

According to a feature of the invention the synthons V may be prepared advantageously from 2-ketoglutaric acid IX which is successively converted to diester X, derivative XI (in which X, Y, $R_1$ and $R_2$ have the above indicated meanings), monoester XII, the latter compound being converted to the aldehyde-ester V by a process including, if desired, reduction to alcohol-ester XIII by means of diborane followed by oxidation of the alcohol group by means of pyridinium chlorochromate.

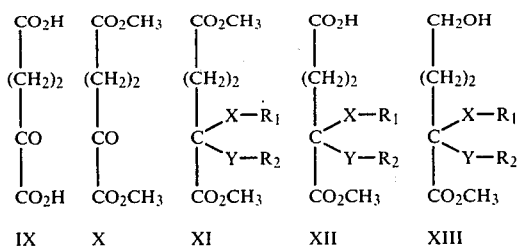

IX   X   XI   XII   XIII

The following examples in which $R=CH_3$; $X, Y=O$; $R_1, R_2=CH_3$; $Z=H$ illustrates the features of the present invention without restricting the scope thereof.

(1) Preparation of the diester ketal XI ($X=Y=O$; $R_1=R_2=CH_3$)

The 2-ketoglutaric acid IX (26.2 g- 179 millimoles) is dissolved into 100 ml of methanol, and 2 ml of concentrated sulphuric acid are added. After 4 hours reflux heating, 30 ml of methyl orthoformate are added and after 4 hours reflux heating the reaction mixture is treated with water and chloroform. The residue still containing a little amount of ketone is taken up with 50 ml of dry methanol, 25 ml of methyl orthoformate and 1 ml of $H_2SO_4$.

After 8 hours reflux heating, the mixture is poured into 500 ml of water saturated with $Na_2CO_3$ and extracted with 200 ml and then with $2 \times 100$ ml of $CHCl_3$. The organic phases are collected, dried on $Na_2SO_4$, filtered and evaporated under vacuum.

The residue is redistilled under vacuum.
One obtains 28.8 g of compound XI as a limpid liquid.
Boiling point: 100°-115° C. (about 1 mm)
IR spectrum: 2810, 1750, 1430, 1100 cm$^{-1}$
NMR spectrum: (CDCl$_3$) 3.80 (s) 3H; 3.75 (s) 3H; 3.25 (s) 6H; 2.25 (m:AA' BB') 4H (2) Preparation of the monoacid XII ($X=Y=O=$; $R_1=R_2=CH_3$)

The diester XI (28.4 g-129 millimoles) is dissolved into a mixture of 120 ml of methanol and 50 ml of $H_2O$.

A solution of 5.16 g of NaOH(129 millimoles- 1 equivalent) in 25 ml of $H_2O$ is added and the mixture is stirred 44 hours at room temperature.

The mixture is then neutralized by means of 7.78 g of glacial acetic acid (129 millimoles-1 equivalent) and extracted by means of $3 \times 150$ ml of ethyl acetate.

The organic phases are collected, dried and evaporated under vacuum. The residue is rectified by distillation. One recovers 2.2 g of the starting product XI (boiling at 110° C./1 mm) and 18.5 g of the desired monoacid XII: boiling point 140° C./0.2mm
IR spectrum: 3300, 2830, 1750, 1700, 1060 cm$^{-1}$
NMR spectrum (CDCl$_3$): 8.90 (s) 1H; 3.80 (s) 3H; 3.28 (s) 6H; 2.30 (m, AA' BB') 4H (3) Preparation of the ester-alcohol XIII ($X=Y=O$; $R_1=R_2=CH_3$)

The acid XII (3.64 g-17.6 millimoles) is dissolved into 50 ml of freshly distilled, dry tetrahydrofuran. To that solution one adds quickly 1.50 g (39.6 millimoles) of finely divided NaBH$_4$ and one cools to 5° C. BF$_3$ etherate (6.5 ml; 7.49 g; 52.8 millimoles) is then added drop by drop to the solution maintained under nitrogen coverage. After one hour stirring, the excess of $B_2H_6$ is destroyed by means of a glacial acetic acid solution in dry tetrahydrofuran. The reaction mixture is poured into 300 ml of brine and extracted with 200 ml and then with $2 \times 100$ ml of chloroform.

The extraction solution is washed with 150 ml of a solution saturated with $Na_2CO_3$, dried on $Na_2SO_4$, filtered and the filtrate is evaporated under vacuum.

One obtains 3.14 g of compound XIII as a colourless oil.
IR spectrum: 3480, 2830, 1745, 1005 cm$^{-1}$
NMR spectrum (CDCl$_3$): 3.80 (s) 3H; 3.60 t J=7H$_z$, 2H$_z$ 3.30 (s) 1H; 3.25 (s) 6H; 1.95 and 1.50 4H complex multiplet.

(4) Preparation of the aldehyde ketal V ($R_1=R_2=CH_3$; $X=Y=O$)

A suspension is prepared consisting of 7 g of pyridinium chlorochromate (32.6 millimoles-2 equivalents) and 2.67 g of sodium acetate (32.6 millimoles) in 100 ml of dry $CH_2Cl_2$.

Said suspension is cooled to 0° C. and the alcohol XIII (3.14 g; 16.3 millimoles) dissolved in 50 ml of $CH_2Cl_2$ is added drop by drop. After two hours at 0° C. and 24 hours at room temperature, the chromium salts are precipitated by means of 250 ml of dry ether. The solution is filtered on a column of 40 g of Florisil. The solid residue is washed with $2 \times 250$ ml of dry ether and the extract thus obtained is filtered on the Florisil column. After evaporation, one obtains 2.10 g of the desired aldehyde V.
IR spectrum: 2840, 2740, 1750, 1720 cm$^{-1}$
NMR spectrum (CDCl$_3$): 9.75 (bt) 1H; 3.80 (s) 3H; 3.25 (s) 6H; 2.10-2.50 m 4H;

(5) Tetrahydrocarboline VI
($Z=H; R=CH_3; R_1=R_2CH_3; X=Y=O$)

The aldehyde ketal V (4.74 g) and N-methyl tryptamine (formula IV: $Z=H$; $R=CH_3$) (4.35 g) are dissolved into 50 ml of dry benzene. 5 ml of glacial acetic acid are added and the mixture is reflux heated for 4 hours. The usual treatment provides 9.06 g of residue which is purified on a column of silica. Eluent CHCl$_3$-methanol 95/5.

One obtains 3.96 g of pure tetrahydrocarboline VI
IR spectrum: 3280 (NH), 2840 (OMe), 2800 (NMe), 1750, 1460, 1200, 1100, 750 cm$^{-1}$
NMR spectrum (CDCl$_3$): 8.20 1H; 7.0–7.60 (m) 4H; 3.78 (s) 3H; 3.50 (m) 1H; 3.25 (s) 3H; 3.20 (s) 3H; 2.80 (m) 4H; 2.45 (s) 3H; 1.90 (m) 4H;

(6) Preparation of chanodesethylapovincamine I
($R=CH_3$; $Z=H$)

The tetrahydrocarboline VI (4.5 g) is dissolved into 5 ml of chloroform to which 2 ml of trifluoroacetic acid are added. The reaction is followed up by NMR. After 16 hours at 55° C. and conventional treatment, one obtains 3.2 g of compound I as a homogeneous less polar product by thin layer chromatography.
IR spectrum: 2960, 2900, 2840, 2800, 1720, 1640, 1620, 1460, 1300, 1250, 740 cm$^{-1}$
NMR spectrum (CDCl$_3$): 7.60–7.00 (m) 4H; 6.45 (dd,J=7Hz, 3Hz) 1H; 3.95 (s) 3H; 2.50 (s) 3H.

(7) Preparation of chanodesethylapovincamine I
(R=CH₂CH₃; Z=H)

In the hereabove described manner, the compound of formula I in which R represents an ethyl group is prepared.

It has the following properties:

Melting point: base 120°–121° C.; hydrochloride 194°–195° C.

Mass spectrum: 296 M+(m/e) calculated for $C_{18}H_{20}N_2O_2$

IR spectrum: 2960, 2900, 2840, 2800, 1720, 1640, 1620, 1440, 1300 cm⁻¹

NMR spectrum (CDCl₃,δ): 7.6–7.00 (m, 4H); 6.45 (dd, J=7Hz, 3Hz, 1H); 4.0 (S, 3H); 1.66 (t, 3H)

The invention also relates to the industrial applications and inter alia the pharmaceutical uses of the above described products.

The compounds of formula I have been subected to pharmaceutical tests which showed interesting properties, more particularly anti-anoxic, psychotropic and oxygenating properties.

Acute toxicity

The compounds of the invention were administered by intragastric or by intravenous route to Charles River stock mice. The lethal doses for 50% (LD₅₀) were determined graphically according to the method of Lichtfield and Wilcoxon (J.Pharmacol.Exp. Therap. 1946, 96, 99).

Hypobaric anoxia test on mice

Charles River stock mice of the same sex, weighting about 20±2 g are shared into three lots of 10 animals each. The lots 1 and 2 comprise treated animals, i.e. those having received either a substance to be tested. The third lot comprises control animals.

The compounds examined are administered p.o. 30 minutes before the experiment.

The animals are placed in an atmosphere improverished in oxygen by creating a partial vacuum (190 mm Hg, corresponding to 5.25% oxygen), in about 30 seconds.

The survival time of the mice is measured with a chronometer. Said time is increased by the agents capable of enhancing oxygenation of tissues and more particularly brain oxygenation.

Under the above described conditions, the dose which provides a 50% increase of the average survival time of the animals may be expressed as the 50% effective dose (here abbreviated as ED₅₀).

The results obtained with the compound of formula I in which R represents ethyl and Z represents a hydrogen atom are gathered in the following Table I.

TABLE I

| LD₅₀(mg/kg) | ED₅₀(mg/kg) | LD₅₀/ED₅₀ |
| --- | --- | --- |
| p.o. 1125 | 225 | 5 |
| i.v. 55 | | |

In addition, a substantial increase of vertebral flow rate was noticed upon dogs previously anesthetized with sodium pentobarbital (30 mg/kg i.v.). More particularly a does of 5.5 mg/kg i.v. of N-ethylchanodesethylapovincamine causes a 50 to 100% increase of vertebral flow rate. Said effect on the flow rate is selective, the increase of femoral flow rate being negligible.

For their therapeutical use, the compounds of the invention will be provided in the form of base or salt of addition to pharmaceutically acceptable acids.

The compounds of the invention, having both anti-anoxic and psychotropic activities may be used therapeutically for treating troubles of vigilance, particularly to fight against behavior troubles due to cerebral vascular damages and brain sclerosis in geriatrics. They also may be used as sedatives as well as for treating absences due to cranium injuries and for treating conditions of depression. They may also be used generally for treating cerebro-vascular or cardio-circulatory diseases.

For their therapeutical use, the compounds of formula I may be administered either by digestive route in the form of capsules, tablets, pellets, dragees, cachets, solutions or suspensions or by parenteral route as buffered sterile solutions, prepared beforehand or extemporaneously, in which the active substance, base or salt, is present in an amount of 0.5 mg to 700 mg per unit. The daily dose may vary between 1 mg and 500 mg according to disease.

For therapeutical use, the compounds of the invention are provided as pharmaceutical compositions containing as the active substance at least one of said compounds possibly in admixture with other active substances and adjuvants, diluents, vehicles or carriers as well as dyestuffs sweeteners, preserving agents, anti-oxidizers, etc., which are commonly used in pharmaceutics.

The preparation of pharmaceutical or galenical formulations is effected according to usual methods substantially consisting of incorporating or admixing the active substance or substances with the adjuvants used.

If the compounds are administered in the form of their acid addition salts, it is necessary to use pharmaceutically acceptable acids which are well-known in pharmaceutics.

What I claim is:

1. Indole derivatives of the general formula

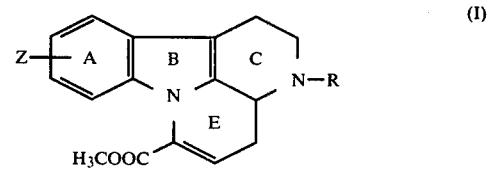

in which R represents a hydrogen atom or a linear or branched, saturated or unsaturated alkyl group having 1 to 5 carbon atoms or a benzyl (i.e. CH₂—C₆H₅) group and Z represents either a hydrogen atom or an alkyl, hydroxy, acyloxy, carbamate or methoxy radical or a halogen atom, said compounds being in the form of bases or salts of organic or inorganic acids and in the form of any desired optical isomer or racemic mixture.

2. A compound according to claim 1 wherein in the formula I R represents a methyl group and Z represents a hydrogen atom.

3. A compound according to claim 1 wherein in the formula I R represents an ethyl group and Z represents a hydrogen atom.

4. A drug for treating cardio-circulatory and cerebrovascular diseases, which contains a therapeutically effective amount of at least one compound according to claim 1 in the form of a base or a pharmaceutically acceptable acid addition salt, together with a pharmaceutically acceptable adjuvant, vehicle or carrier.

5. A drug according to claim 4, in the form of tablets, capsules or injectable solutions containing 0.5 mg to 700 mg of active substance per unit possibly in admixture with adjuvants, diluents, vehicles or carriers commonly used in pharmaceutics.

* * * * *